(12) United States Patent
Schramm et al.

(10) Patent No.: US 6,379,911 B2
(45) Date of Patent: *Apr. 30, 2002

(54) ENZYME DETECTION/ASSAY METHOD AND SUBSTRATES

(75) Inventors: Vern L. Schramm, New Rochelle, NY (US); Richard Hubert Furneaux, Wellington (NZ); Peter Charles Tyler, Wellington (NZ); Keith Clinch, Wellington (NZ)

(73) Assignees: Albert Einstein College of Medicine of Yeshiva University, Bronx, NY (US); Industrial Research Limited, Lower Hutt (NZ)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,808
(22) PCT Filed: Feb. 24, 1997
(86) PCT No.: PCT/NZ97/00021
   § 371 Date: Feb. 22, 1999
   § 102(e) Date: Feb. 22, 1999
(87) PCT Pub. No.: WO97/31008
   PCT Pub. Date: Aug. 28, 1997

(30) Foreign Application Priority Data
Feb. 23, 1996 (NZ) .................. 286059

(51) Int. Cl.[7] ............. C12Q 1/34; C12Q 1/04; C07D 307/04
(52) U.S. Cl. ............. 435/18; 435/34; 549/429; 549/475
(58) Field of Search ........... 435/18, 34, 805, 435/810, 94.61; 536/22.1, 18.7; 549/429, 475

(56) References Cited

U.S. PATENT DOCUMENTS

| | | | |
|---|---|---|---|
| 3,784,444 A | * 1/1974 | Nakayama et al. | 195/28 |
| 4,308,348 A | * 12/1981 | Monget | 435/38 |
| 4,385,112 A | * 5/1983 | Misaki et al. | 435/6 |
| 5,525,711 A | * 6/1996 | Hawkins et al. | 536/22.1 |
| 5,631,127 A | * 5/1997 | Sundrehagen | 435/4 |

OTHER PUBLICATIONS

Abstract only of Claeyssens et al.*
Biochemistry, second edition. Voet and Voet, eds. John Wiley and Sons, New York. (1995). No month.*
Cherian et al. Models for nucleoside glycosylase enzymes. J. Am. Chem. Soc. 112, pp. 4490–4498 (May 1990).*
Godsey et al. Rapid identification of Enterobacteriaceae with microbial enzyme profiles. J. Clin. Microbiol. 13 (3), pp. 483–490. (Mar. 1981).*
Hespell et al. Purification and characterization of an α–L–arabinofuranosidase from Butyrivibrio fibrosolvens GS113. Appl. and Environ. Microbiol. 58(4), pp. 1082–1088. (Apr. 1992).*
Johnson et al. Cloning, expression and nucleotide sequence of the gene fragment encoding an antigenic portion of the nucleoside triphosphate hydrolase of Toxoplasma gondii. Gene 85, pp. 215–222. (1989). No month found.*
Parkin et al. Nucleoside hydrolase from Crithidia fasciculata. J. Biol. Chem. 266 (31), pp. 20658–20665. (Nov. 1991).*
Schyns et al. Production, purification and characterization of an α–L–arabinofuranosidase from Bacteroides xylanolyticus X5–1. Appl. Microbiol. Biotechnol. 42(4), pp. 548–554. (Dec. 1994).*
Vance et al. Synthesis and hydrolysis kinetics of 1–O–[p–(N,N,N–trimethylammonio)phenyl]–β–D–ribofuranoside. J. Org. Chem. 58(8), pp. 2343–2344. (Apr. 1993).*

* cited by examiner

Primary Examiner—Michael P. Woodward
Assistant Examiner—Marjorie A. Moran
(74) Attorney, Agent, or Firm—Amster, Rothstein & Ebenstein

(57) ABSTRACT

The invention relates to a method of detecting and/or assaying nucleoside hydrolases or nucleoside phosphorylases using a chromogenic substrate. Preferred chromogenic substrates have formula (I) where X is OH, or H, and Y is the residue of Y—OH where Y—OH is a chromophore or a compound readily converted to a chromophore and the substrates are hydrolyzed by the nucleoside hydrolase to yield ribose or 2-deoxyribose plus Y—OH. Alternatively, those substrates may be phosphorylysed by nucleoside phosphorylase to yield ribose-1-phosphate plus Y—OH. The methods may be used to detect and/or assay parasites in biological samples.

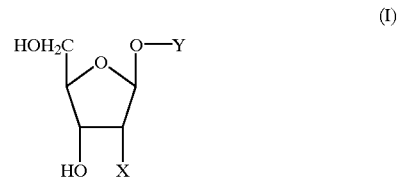

(I)

31 Claims, No Drawings

ENZYME DETECTION/ASSAY METHOD AND SUBSTRATES

The invention relates to an enzyme detection method and to its use in detection of parasites.

BACKGROUND ART

Protozoan parasites have an adverse effect on the health of human and animal populations in a large number of countries. Problems presented by protozoan parasites are particularly of concern in tropical areas of the world where modern diagnostic methods are often not easily accessible.

Nucleoside hydrolases are enzymes which hydrolyse nucleosides between the ribose or deoxyribose and the purine or pyrimidine base groups. A number of different types of nucleoside hydrolases are known. N-Ribohydrolases hydrolyse ribonucleosides and N-deoxyribohydrolases hydrolyse deoxyribonucleosides. Within each of these two general groups of enzymes are enzymes of differing specificities.

Among the well-characterized N-ribohydrolases, specificity is high for the ribosyl group but varies for the leaving group purine or pyrimidine. The inosine-uridine nucleoside hydrolase (IU-nucleoside hydrolase) from the trypanosome *Crithidia fasciculata* hydrolyzes all of the naturally occurring purine and pyrimidine nucleosides with similar catalytic efficiencies. The guanosine-inosine enzyme (GI-nucleoside hydrolase) from the same organism has a strong preference for the eponymous substrates and is nearly inert with the pyrimidine nucleosides[1,2,3,4]. AMP Nucleosidase from bacterial sources is highly specific for the adenine base, and the 5'-phosphoryl is required for significant hydrolytic rates[5,6]. Nucleoside phosphorylases have a similar mechanism to nucleoside hydrolases and, for example, purine nucleoside phosphorylase is specific for inosine and guanosine substrates and activates phosphate or arsenate anions to attack C1 of the nucleosides.

It is an object of the invention to provide a method of detecting and/or assaying for the presence of certain enzymes, especially those of parasites in samples taken from parasitised humans and animals.

SUMMARY OF THE INVENTION

In one aspect the invention provides a method of detecting and/or assaying nucleoside hydrolases using a chromogenic substrate.

Preferably the chromogenic substrates have the formula:

(FORMULA I)

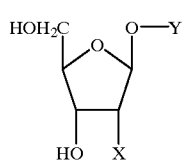

where X is OH or H, and Y is the residue of Y—OH where Y—OH is a chromophore or a compound readily converted to a chromophore and the substrates are hydrolysed by the nucleoside hydrolase to yield ribose or 2-deoxyribose plus Y—OH.

Preferably the chromogenic substrates are of Formula I wherein X and Y are as defined and the substrates are phosphorylysed by the nucleoside phosphorylase to yield ribose-1-phosphate or 2-deoxyribose-1-phosphate plus Y—OH.

Y may be chosen so that Y—OH is a compound absorbing in the visible or TV light, readily measured at wavelengths greater than 300 nm, preferably greater than 340nm.

Preferably Y—OH is 6-hydroxynicotinamide or 2-hydroxypyridine -4-carboxamide.

Y may be chosen so that Y—OH is a chemiluminescent compound eg luminol which when released and oxidized by chemical or enzymatic means emits light.

Alternatively Y—OH may be a compound readily converted to a coloured compound eg by reaction with a diazonium salt eg α-naphthol.

More preferably Y—OH is a fluorescent compound eg 4-methylumbelliferone or fluoroscein.

Most preferably Y—OH is a coloured compound eg phenolphthalein, p-nitrophenol, thymolphthalein, 2-nitrophenol, 2-hydroxy-5-nitropyridine.

It is preferred that Y—OH can be measured in the presence of the compound of Formula I by virtue of Y—OH absorbing or fluorescing to a greater extent than the compound of Formula I at certain wavelengths. Generally this will be by virtue of Y—OH ionising and being in equilibrium with quinonoid-like forms.

A particularly preferred substrate is p-nitrophenyl β-D-ribofuranoside. Also particularly preferred is 4-pyridyl β-D-ribofuranoside. Further particularly preferred substrates are 4-methylumbelliferyl β-D-ribofuranoside (4-methylcoumarin-7-yl β-D-ribofuranoside) and 2-(5-nitropyridyl) β-D-ribofuranoside.

According to another aspect of the invention, there is provided a method for detecting and/or assaying for parasites especially protozoa in samples obtained usually from humans or animals using a chromogenic substrate, preferably of Formula I.

More preferably the chromogenic substrate is one where Y—OH is fluorescent or coloured.

Another preferred type of substrate is one where Y—OH is chemiluminescent eg luminol.

According to a further aspect of the invention there is provided a kit containing materials for detection or assay of hydrolysis of the chromogenic substrate, preferably of Formula I, by enzymes in a biological sample. Preferred kits comprise the chromogenic substrate in dry form, together with a buffer. Other components eg a cell-lysing agent may also be included.

According to a further aspect of the invention there is provided a dipstick containing a chromogenic substrate, preferably of Formula I, for use in detecting nucleoside hydrolases.

According to a further aspect of the invention there are provided novel compounds of the invention of formula I. In this aspect of the invention X and Y are as previously defined except the known compounds α-naphthyl β-D-ribofuranoside, 4-methylcoumarin-7-yl 2-deoxy-p-β-ribofuranoside, β-nitrophenyl β-D-ribofuranoside, p-aminophenyl β-D-ribofuranoside, 5-amino-6-chloro-3-pyridazinyl β-D-ribofuranoside, 4-chlorophenyl β-D-ribofuranoside, phenyl β-D-ribofuranoside, 4-methoxyphenyl β-D-ribofuranoside, 4-hydroxyphenyl β-D-ribofuranoside, 4-(N,N,N-trimethylammonio )phenyl β-D-ribofuranoside, 4-acetylphenyl β-D-ribofuranoside and the β-D-ribofuranosides of L-DOPA and L-α-methyl-DOPA and the N-acetyl methyl esters of the abovementioned DOPA derivatives are not included in this aspect. The exceptions are not known as chromogenic substrates or for use in assay of parasites. Generally the chromogenic group is not coloured when present in the compound of Formula I but is readily detectable when that compound is hydrolysed to give Y—OH.

Preferred compounds are those defined above in which Y is an optionally substituted pyridyl group or a nitrophenyl group.

Particularly preferred novel compounds of the invention include 3-trifluoroacetamidophenyl β-D-ribofuranoside, 3-aminophenyl- β-D-ribofuranoside, 1-tetralone-5-yl β-D-ribofuranoside, 3-( 4-hydroxyphenyl)-1-(3H)-isobenzofuranone-3-(phen-4-yl) β-D-ribofuranoside, 2-nitrophenyl β-D-ribofuranoside, 4-methylcoumarin-7-yl β-D-ribofuranoside, 3-pyridyl β-D-ribofuranoside, 4-pyridyl β-D-ribofuranoside, 2-(5-nitropyridyl) β-D-ribofuranoside, 5-quinolyl β-D-ribofuranoside, the β-D-ribofuranoside of luminol, p-nitrophenyl 2-deoxy- β-D-erythro-pentofuranoside, 3-carboxamido-6-pyridyl β-D-ribofuranoside, and 4-forymylphenyl β-D-ribofuranoside.

In a further aspect of the invention there is provided a method of preparing a chromogenic substrate of the invention.

According to a further aspect the invention may be directed to a method to detect or assay for the presence of nucleoside phosphorylases using a chromogenic substrate.

DETAILED DESCRIPTION OF THE INVENTION

One group of preferred chromogenic substrates have a β-D-ribofuranosyl group attached through a β-O-ribosidic linkage to a chromogenic group.

In a preferred embodiment the chromogenic substrate is a compound of Formula I wherein X=OH. The group Y is as defined under Formula I. Preferably the chromophore Y—OH is selected from the group of phenolphthalein, p-nitrophenol, 4-methylumbelliferone, α-naphthol, thymolphthalein, 2-nitrophenol, 2-hydroxy-5-nitropyridine, 6-hydroxynicotinamide, 2-hydroxypyridine-4-carboxamide and fluorescein. Other chromophores as will be known in the art may also be used.

In this specification the term "chromogenic group" is used to refer to a group in a nucleoside hydrolase substrate bound to the sugar moiety which, when enzymnatically removed from the substrate, forms a compound which is readily detectable by its visible or UV absorption or by its fluorescence. It may be detectable either as released or after pH alteration, or after a subsequent reaction. The term "chromophore" is used for the readily detectable product as released and/or as detectable. The term "chromogen" as used in chemical names, eg 1-O-chromogen derivatives, indicates that the relevant group is a "chromogenic group" as defined above. It is preferred that the "chromophore" is readily detectable by its visible absorption, or alternatively, by its fluorescence, but the definition herein also includes other molecules. The term "chromogenic substrate" is used to refer to a substrate containing a "chromogenic group".

In general it is preferred that the chromophore Y—OH is coloured or can be converted to a coloured form simply by altering the pH. Especially preferred chromophores include p-nitrophenol, phenolphthalein, thymolphthalein and 2-hydroxy-5-nitropyridine. For applications where the enzyme levels are low, a fluorescent chromophore may be preferred, especially 4-methylumbelliferone.

The invention is not limited solely to the detection of nucleoside hydrolases. Nucleoside phosphorylases are not hydrolases as they use phosphate as the nucleophile rather than water. The result is a yield of ribose-l-phosphate rather than ribose. Nucleoside phosphorylases have a similar mechanism to nucleoside hydrolases and can be detected using the method of the present invention.

On hydrolysis the chromogenic group is released from the molecule and may be conveniently measured as the chromophore. Phenolphthalein released by hydrolysis gives a red colour, p-nitrophenol and 2-nitrophenol a yellow colour and thymolphthalein a blue colour. 4-Methylumbelliferone and fluorescein are intensely fluorescent products. α-Naphthol will react with diazonium salts to give highly coloured dyes when released from the substrate. 2-Hydroxy-5-nitropyridine, 6-hydroxynicotinamide and 2-hydroxypyridine-4-carboxamide are further compounds which when released from a substrate are readily measurable when the —OH is ionised. Intensity of colour or fluorescence increases on making the hydrolysate alkaline to fully ionise the phenolic groups for some of the above compounds as is well known in the art.

A number of the preferred substrates yield a Y—OH which is a nitrophenol, or a hydroxypyridine. Preferred substrates include the β-D-ribofuranosides of 2-nitrophenol, 4-methyl umbelliferone, 3- and 4-hydroxypyridine, 2-hydroxy-5-nitropyridine, luminol, 6-hydroxynicotinamide and 4-formylphenol.

A particularly preferred substrate is p-nitrophenyl β-D-ribofuranoside ("nitrophenylriboside"). Another particularly preferred substrate is 4-pyridyl β-D-ribofuranoside ("4-pyridylriboside").

The enzyme assay/detection method may be used in a manner which takes advantage of the fact that the chromogenic substrates are considerably more efficiently hydrolysed by some nucleoside hydrolases than others.

In another aspect of the invention chromogenic substrates are hydrolysed by parasite nucleoside hydrolases releasing the chromophore allowing the detection or assay of the parasite especially in mammalian samples. Among the parasites which may be detected/assayed by this type of method are Giardia, Trichomonas, Leishmania, Trypanosoma, Crithidia, Herpetomonas, and Leptomonas, especially Trypanosoma. Also especially preferred for use in this method are Giardia. Toxoplasma and Neophora may also be detected/assayed by the method of the invention. As will be apparent to those skilled in the art, the method can be advantageously applied with any parasite containing one or more nucleoside hydrolases which can catalyse hydrolysis of the chromogenic substrate efficiently enough to be detectable/measurable in a mammalian sample.

*Trypanosoma cruzi, Giardia intestinalis,* and *Trypanosoma vaginalis* are particularly suitable for assay/detection by the method of the invention.

In another aspect of the invention, deoxyribonucleoside hydrolases and protozoan parasites containing deoxyribonucleoside hydrolases can be detected by analogous methods when the chromogenic substrates used contain a 2-deoxy-β-D-ribofuranosyl moiety rather than a β-D-ribofuranosyl moiety. In preferred embodiments of this aspect the chromogenic substrate is a compound of formula I wherein X=H. The chromogenic group Y is as defined under formula I. Preferably the chromophore when released from the substrate is selected from one of phenolphthalein, p-nitrophenol, 4-methylumbelliferone, α-naphthol, thymolphthalein. 2-nitrophenol, 2-hydroxy-5-nitropyridine, 6-hydroxynicotinamide, 2-hydroxypyridine-4-carboxamide and fluorescein, especially p-nitrophenol and 4-methylumbelliferone.

Chromogenic substrates may be prepared starting with a ribosyl ester such as 1-O-acetyl-2,3,5-tri-O-benzoyl-β-D-ribofuranose which is commercially available from Aldrich. This can be coupled to a chromophore molecule with a free OH. This may be achieved using a Lewis Acid such as $BF_3.(OEt)_2$ as catalyst to give a 1-O-chromogen derivative. The 1-O-chromogen-triesterified-ribose compound (eg 1-O-chromogen-tri-O-benzoyl ribose) can be extracted and purified and the ester (eg benzoate) groups removed by hydrolysis (eg by stirring overnight in methanol adjusted to about pH 10 with aqueous sodium hydroxide). If so desired, phosphorylation at the five position of the ribofuranose moiety may be accomplished by reaction with N,N-diethyl-1,5-dihydro-2,4,3-benzodioxaphosphepin-3-amine in tetrazole-acetonitrile followed by oxidation with m-chloroperoxybenzoic acid. The resulting 5-O-(o-xylylenephosphato)-β-D-ribofuranoside compound may be converted to the corresponding ribofuranoside 5-O-phosphate by hydrogenation e.g. over Pd/C in ethanol followed by neutralisation with aqueous sodium hydroxide.

Reaction scheme 1 includes the above general reaction scheme as Method A.

Alternative syntheses are also possible, for example, by Michael or Koenigs-Knorr type synthesis involving O-protected ribofuranosyl halides (eg acetates, benzoates) and reaction with phenolate salt or phenol and heavy metal catalyst eg Ag(I), Hg(II) salts or oxide. The halide may be a chloride, bromide or a fluoride (eg see Method B of Reaction Scheme 1).

REACTION SCHEME 1
GENERAL REACTION SCHEME FOR THE PREPARATION OF
β-D-RIBOFURANOSIDES

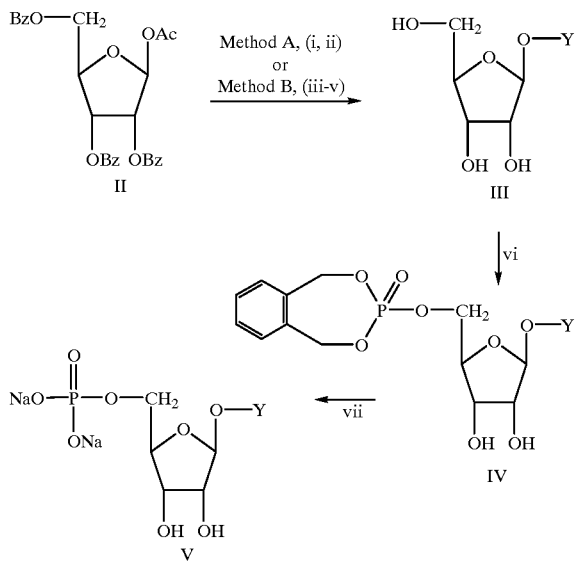

Reagents:
(Method A): i, Y—OH, $BF_3.OEt_2$; ii, NaOH, $H_2O$, MeOH; (Method B); iii, $TiCl_4$, $CH_2Cl_2$; iv, Y—O⁻Ag⁺, Toluene; v, $K_2CO_3$, MeOH then Amberlite IRC-50 (H⁺) resin; vi, N,N-diethyl-1,5-dianhydro-2,4,3-benzodioxaphosphepin-3-amine, 1H-tetrazole, then MCPBA; vii, $H_2$, Pd/C, EtOH, then NaOH.

Y—OH or its silver salt (Y—O⁻Ag⁺) is a chromophore as defined in the specification.

REACTION SCHEME 2
GENERAL REACTION SCHEME FOR THE PREPARATION OF
2-DEOXY-β-D-RIBOFURANOSIDES

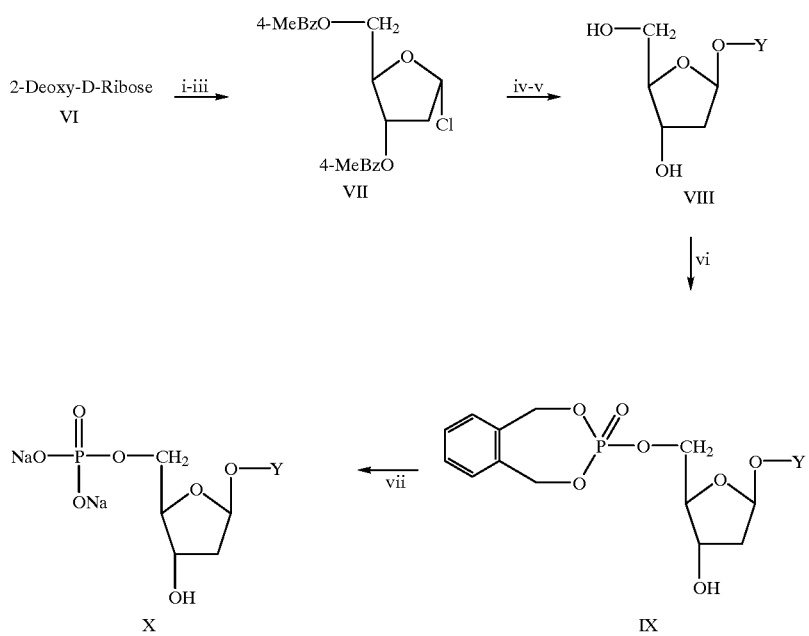

Reagents:

i, MeOH, HCl; ii, 4-MeBzCl, Pyridine; iii, HCl, AcOH; iv, Y—O⁻Na⁺, DMF; v, $K_2CO_3$, MeOH; vi, N,N-diethyl-1,5-dianhydro-2,4,3-benzodioxaphosphepin-3-amnine, 1H-tetrazole, then MCPBA; vii, $H_2$, Pd /C, EtOH, then NaOH.

Y—O⁻Na⁺ is the sodium salt of Y—OH, a chromophore as defined in the specification.

Corresponding deoxy-β-ribofuranosyl compounds may be prepared using the above methods but with the ribofuranosyl starting materials replaced with the corresponding 2-deoxyribofuranosyl compounds. A preferred method is shown in reaction scheme 2.

Generally in the method of the invention for detection/assay of parasites, the samples to be tested are brought into contact with the substrate at an appropriate pH and the reaction is allowed to proceed. The reaction may take place in a spectrophotometer cuvette to which the chromogenic substrate has been added in an appropriate buffer. The choice of buffer and pH will be influenced by a number of factors including the pH activity profile of the enzyme and the particular parasites under investigation. The choice of buffer and pH can readily be determined by those skilled in the art. The pH will generally be in the range 7–8.5. When a substrate such as nitrophenylriboside or phenolphthalein riboside is being used, use of slightly alkaline pH values may be preferred as, when the chromophore is released, p-nitrophenol and phenolphthalein will then be more coloured. Where a chromophore is coloured at the pH of the reaction its release from the riboside can be directly monitored in a spectrophotometer for example. Where the reaction is carried out at a pH in which the chromophore is not coloured, it may be necessary to allow the reaction to proceed for some time and then adjust the pH to observe the chromophore at a pH where it is coloured.

In a preferred method the sample is brought into contact with p-nitrophenylriboside at about pH 8 and the reaction is monitored by appearance of colour of a nitrophenolate ion formation. The colour may be monitored visually or by measuring absorption at 400 nm.

Where the chromophore is α-napthol, the reaction is allowed to proceed and then after a time the chromophore is reacted with a diazonium salt to produce the coloured compound which is subsequently used to measure the extent of the reaction.

Where the chromophore is luminol, the luminol released in the enzyme reaction is subsequently oxidized by chemical on enzymic means known in the art and the emitted light from the chemiluminescence obtained is measured.

The invention may be practised with many variations so long as the critical feature of a substrate of a nucleoside hydrolase or phosphorylase, where the base is replaced by a chromogenic group, is present. Generally the chromogenic group is not coloured when present on the substrate but is when released by the action of the enzyme or else is otherwise readily detected once liberated from the substrate. Those skilled in the art will appreciate that this may be carried out with many variations.

The reaction need not necessarily be carried out in a test tube or cuvette. The reagents may be included in test strips whereby biological sample is added to the test strip and colour is generated if the sample contains parasites containing one or more enzymes which hydrolyse the chromogenic substrate. For convenience the test strip may form part of a dipstick. Such dipsticks may be prepared according to methods well known in the art.

The invention may be carried out with many sample types, e.g. biological samples including blood or serum samples. The samples may be taken from a mammal (e.g a human, bovine, pig, goat, sheep or horse) but may also be taken from other species (eg fish species or from the environment).

For some samples minimal preparation is necessary. For example the assay for *Trypanosoma cruzi*, the causative agent of Chagas disease, may be carried out on a blood lysate containing one microlitre of infected blood. The lysate may be prepared by mixing blood with an equal volume of 1% nonionic detergent. Other sample preparation methods may be used. For example samples may be disrupted by use of sonication.

In another aspect of the invention, advantage can be taken of the different substrate specificity of the different parasite enzymes to assist in determining the nature of a parasite infection. Differences in specificities are illustrated in the Examples by comparison of kinetic data from IU-nucleoside hydrolase from *Crithidia fasciculata* and IAG-nucleoside hydrolase from *Trypanosoma brucei brucei*. The compound p-nitrophenylriboside is a particularly good substrate for the former but not the latter. In contrast, 4-pyridyl riboside and 2-(5-nitropyridyl) riboside show lower activity with the former enzyme than does nitrophenylriboside, but substantially greater activity with the latter than does the nitrophenylriboside.

Kits containing a chromogenic substrate of Formula (I) optionally together with a buffer and/or materials for processing the biological sample prior to assay/detection (eg a cell-lysing solution) are included within the invention. Preferably the substrate is in a dry form to minimise hydrolysis during storage.

EXAMPLES

The following examples further illustrate practice of the invention. Ratios of solvents are by volume unless otherwise indicated.

Experimental

N.m.r. spectra were recorded on a Bruker AC-300 instrument at 300MHz (H) or 75 MHz ($^{13}$C) and referenced to TMS ($^1$H nmr, δ0.00), $CD_3OD$ ($^{13}$C nmr, δ49.0), $d_6$-DMSO ($^{13}$C nmr, δ40.9) or as otherwise indicated. The $^{13}$C nmr resonance values are followed in brackets by the abbreviations s, d, t or q referring to (C), (CH), ($CH_2$) or ($CH_3$) groups respectively, as determined by distortionless enhancement by polarization transfer (DEPT) experiments. For 1H nmr the following abbreviations are used: s (singlet), d (doublet), t (triplet), q (quartet), m (multiplet), br (broad).

Example 1

Stage 1—Preparation of p-nitrophenyl 2,3,5-tri-O-benzoyl-β-D-ribofuranoside

A solution of 1-O-acetyl-2,3,5-tri-O-benzoyl-β-D-ribofuranose (10 g), p-nitrophenol (5.6 g, 2 eq) and boron trifluoride diethyl etherate (1.2 ml, 0.5 eq) in dry dichloromethane (100 ml) was allowed to stand at room temperature overnight. Thin-layer chromatography on silica gel [Eluant EtOAc:CHCl₃:Hexanes 1:2:4] then indicated essentially complete conversion to a slightly less polar material. The solution was washed with aq bicarbonate and processed conventionally. Flash chromatography on silica gel [eluant EtOAc:CHCl₃:Hexanes 1:2:8] then afforded 8.29 g of title compound.

Stage 2' Preparation of p-nitrophenyl β-D-ribofuranoside

The above material (8.29 g) was suspended in methanol (100 ml) and the pH was adjusted to about 10 with aq NaOH. After stirring overnight the solution was homogeneous and thin layer chromatography on silica gel [eluant CHCl$_3$:EtOAc:MeOH 5:2:1] indicated the reaction was complete. The solution was concentrated under reduced pressure, the residue was dissolved in MeOH/CH$_2$Cl$_2$ [about ½ v/v] and filtered through a pad of silica gel. The silica was washed if necessary with CHCl$_3$:EtOAc:MeOH 5:2:2 to elute all of the product. Concentration of the eluate afforded a pale yellow solid contaminated with methyl benzoate. Trituration with EtOAc gave the title compound (2.77 g). Recrystallisation from EtOAc gave material with mp 156–158° C.

Example 2

Preparation of α-naphthyl β-D-ribofuranoside

Stage 1. Preparation of α-naphthyl 2,3,5-tri-O-benzoyl-β-D-ribofuranoside

A solution 1-O-acetyl-2,3,5-tri-O-benzoyl-β-D-ribofuranose (500 mg, 0.99 mmol), α-naphthol (428 mg, 3.00 mmol) and boron trifluoride diethyletherate (141 mg, 0.99 mmol, 125 μl) in dry dichloromethane (5 ml) was stirred at room temperature under argon for 16 hours. The mixture was worked up as for Stage 1 of Example 1 and purified by flash chromatography on silica gel (eluting with dichloromethane:hexanes, 3:2) to afford the title compound contaminated with α-naphthol. The latter was removed by dissolving the residue in ethyl acetate and washing with 10% aqueous sodium hydroxide solution, which after conventional processing, gave 136 mg, 23% of product as a yellow gum.

Stage 2. Preparation of α-naphthyl β-D-ribofuranoside

The product from Stage 1, (130 mg, 0.22 mmol) was dissolved in methanol (3 ml) and the pH adjusted to about 12 by the addition of 10% aqueous sodium hydroxide. After 5 hours, Amberlite IRC-50 (H$^-$) resin was added to neutralize the excess base until pH 5 had been reached, at which point the resin was filtered off. The filtrate was evaporated in vacuo and purified by flash chromatography on silica gel (5% methanol in dichloromethane) to afford the title compound as a colourless crystalline solid (37 mg, 61%) after trituration with dichloromethane.

$^1$H nmr (d$_6$-DMSO) δ ppm; 8.12 (dd, 1H, J=6.8, 2.5 Hz), 7.87 (dd. 1H, J=6.7, 2.3 Hz), 7.54–7.48 (m. 3H), 7.42 (t, 1H. J=7.8 Hz), 7.12 (d. 1H, J=7.5 Hz), 5.67 (s, 1H), 5.40 (d, 1H. J=4.5 Hz), 5.05 (d, 1H, J=6.3 Hz), 4.68 (t, 1H, J=5.4 Hz), 4.23 (t, 1H, J=4.1 Hz), 4.19–4.13 (m, 1H), 4.00–3.95 (m, 1H), 3.62–3.56 (m, 1H), 3.42–3.37 (m, 1H).

$^{13}$C nmr (d$_6$-DMSO) δ ppm; 153.4(s), 135.5(s), 128.8(d), 127.8(d), 127.5(d), 126.8(d), 126.7(s), 123.0(d), 122.3(d), 109.8(d), 107.0(d), 86.1(d), 76.2(d), 72.2(d), 64.2(t).

Example 3

Preparation of 3-Trifluoroacetamidophenyl β-D-Ribofuranoside

Stage 1.—Preparation of 3-Trifluoroacetamidophenyl

A solution of 3-aminophenol (500 mg, 4.58 mmol), trifluoroacetic anhydride (9.62 g, 45.8 mmol, 6.4 ml) and trifluoroacetic acid (10 ml) was stirred at 0° C. for 2 hrs. The excess solvents were evaporated in vacuo to a solid residue which was dissolved in ethyl acetate and washed with saturated aqueous sodium bicarbonate solution. The organic layer was dried over anhydrous magnesium sulfate, evaporated in vacuo and the residue recrystallized from toluene to afford the title compound as colourless needles, 758 mg, 67%, m.p. 133°–135° C.

Stage 2.—Preparation of 3-Trifluoroacetamidophenyl 2,3,5-tri-O-benzoyl β-D-ribofuranoside A solution of 1-O-acetyl-2,3,5-tri-O-benzoyl-β-D-ribofuranose (500 mg, 0.99 mmol), 3-trifluoroacetamidophenol (407 mg, 1.98 mmol) from Stage 1 and boron trifluoride diethyletherate (1.41 g, 9.93 mmol, 1.25 ml) in a mixture of dry dichloromethane (10 ml) and dry tetrahydrofuran (30 ml) was stirred at room temperature under argon for 7 days. Work-up as in Stage 1 of Example 1 and purification by flash chromatography on silica gel (2% acetone in toluene as eluant) gave the title compound as a colourless solid (166 mg, 21%).

Stage 3.—Preparation of 3-Trifluoroacetamidophenyl β-D-Ribofuranoside

The product from Stage 2 (135 mg, 0.21 mmol) was dissolved in methanol (4 ml), 10% aqueous sodium hydroxide was added to raise the pH to about 13, and then the mixture was stirred for 89 hours. The mixture was neutralized with Amberlite IRC-50 (H$^-$) resin to pH 5, filtered and the filtrate evaporated to a solid residue which was further purified by flash chromatography on silica gel (5% methanol in dichloromethane) to give the title 41;D compound as a colourless gum (17 mg, 24%).

$^1$H nmr (CD$_3$OD) δppm; 7.37 (m, 1H), 7.27 (m, 2H), 6.89 (m, 1H), 5.54 (s, 1H), 4.22–4.15 (m, 2H), 4.06 (dt, 1H, J=6.4, 3.6 Hz), 3.73 (dd, 1H, J=11.9, 3.6 Hz), 3.55 (dd, 1H, J=11.9, 6.2Hz).

$^{13}$C nmr (d$_6$-DMSO) δ ppm; 158.3(s), 155.9 (s)(J$_{F-C}$=37 Hz), 138.9(s), 131.2(d), 117.2 (s)(J$_{F-C}$289Hz) 115.6(d), 114.9(d), 110.4(d), 106.7(d). 87.2(d), 76.0(d), 72.0(d), 64.1 (t).

A second product (31 mg) was also obtained which by $^1$H nmr consisted of a 2:1 mixture of the title product together with 3-aminophenyl β-D-ribofuranoside.

Example 4—Preparation of 3-Aminophenyl β-D-Ribofuranoside

The mixture of 3-trifluoroacetamidophenyl β-D-ribofuranoside and 3-aminophenyl β-D-ribofuranoside from Stage 3 of Example 3 (31 mg) was stirred for 16 hours with 3M aqueous sodium hydroxide, evaporated in vacuo then purified by flash chromatography on silica gel (eluting with 15% methanol in dichloromethane) giving the title compound as a gum (4 mg).

$^1$H nmr (CD$_3$OD) δ ppm; 6.96 (t, 1H, J=8.0 Hz), 6.39 (d, 1H, J=2.1 Hz), 6.34 (m, 2 H), 5.47 (s, 1H), 4.17 (dd, 1H, J=6.7, 4.8 Hz), 4.10 (dd, 1H, J=4.7, 0.9 Hz), 4.02 (dt, 1H, J=6.4, 3.7 Hz), 3.71 (dd, 1H, J=11.9, 3.6 Hz), 3.56 (dd, 1H, J=11.8, 6.2 Hz).

$^{13}$C nmr (CD$_3$OD) δ ppm; 159.2(s), 150.2(s), 130.8(d), 110.5(d), 107.1(d), 106.8(d), 104.7(d), 85.6(d), 76.6(d), 72.4 (d), 64.7(t).

Example 5

Preparation of 1-Tetralone-5-yl β-D-Ribofuranoside

Stage 1.—Preparation of 1-Tetralone-5-yl 2,3,5-tri-O-benzoyl-β-D-Ribofuranoside

A solution of 1-O-acetyl-2,3,5-tri-O-benzoyl-β-D-ribofuranose (426 mg, 0.84 mmol), 5-hydroxy-1-tetralone (122 mg, 0.75 mmol) and boron trifluoride diethyletherate (120 mg, 0.84 mmol, 106 μl) in dichloromethane (4 ml) was stirred at room temperature, under argon for 19 hours. Work-up as for Stage 1 in Example 1 then flash chromatography on silica gel (eluting with 2% acetone in toluene) gave the title compound as a colourless oil (308 mg of approx. 51% purity).

Stage 2.—Preparation of 1-Tetralone-5-yl β-D-Ribofuranoside

The product from Stage 1 (308 mg) was stirred with anhydrous potassium carbonate (245 mg, 1.77 mmol) in methanol (5 ml) for 3 hours at room temperature. Evaporation of the solvent in vacuo, then flash chromatography on silica gel (eluting with 7% methanol in dichloromethane) afforded a colourless solid (77 mg) composed of approximately 7 parts title compound and 1 part of the α-anomer of the title compound.

$^1$H nmr (CD$_3$OD) δ ppm; 7.61 (d, 1H, J=7.7 Hz), 7.35 (dd. 1H, J 8.1, 1.0 Hz), 7.25 (t, 1H, J=7.9 Hz), 5.63 (d, 0.13H, J=4.4 Hz, H-1 of (-anomer), 5.56 (s, 0.87H, H-1 of β-anomer), 4.28–4.11 (m, 2H), 4.10–4.05 (m, 1H), 3.74 (dd, 0.87H, J=11.9, 3.6 Hz), 3.69–3.62 (m, 0.13H), 3.56 (dd, 1H, J=11.9, 6.0 Hz), 3.02 (t, 0.26H, J=6.1 Hz), 2.89 (t, 1.74H, J=6.1 Hz), 2.59 (dd, 2H, J=7.0, 6.2 Hz), 2.07 (t, 2H, J=6.4 Hz).

$^{13}$C nmr (CD$_3$OD) δ ppm; 201.2(s)$_{α, β}$, 156.7(s)$_α$, 156.0 (s)$_β$, 137.5(s)$_α$, 136.3(s)$_β$, 135.2(s)$_β$, 131.0(d)$_α$, 128.3(d)$_β$, 128.2(d)$_α$, 122.3(d)$_α$, 121.8(d)$_α$, 121.4 (d)$_β$, 120.9(d)$_β$, 107.5(d)$_β$, 103.5(d)$_α$, 88.3(d)$_α$, 86.3(d)$_β$, 77.1(d)$_β$, 73.9(d)$_α$, 72.8(d)$_β$, 71.6(d)$_α$, 64.9(t)$_β$, 63.7(t)$_α$, 40.2(t)$_α$, 40.1(t)$_β$, 24.6 (t)$_α$, 24.5(t)$_β$, 24.2(t)$_α$, 24.1(t)$_β$.

Example 6

Preparation of p-Aminophenyl β-D-Ribofuranoside

The product from Stage 2 of Example 1 (p-nitrophenyl β-D-ribofuranoside 31 mg, 0.11 mmol) was suspended in methanol (5 ml) containing 10% palladium on carbon (14 mg) and hydrogenated for 16 hrs. The palladium catalyst was filtered off and the solvent evaporated in vacuo to give the title compound as a pale pink gum (23 mg, 82%).

$^1$H nmr (CD$_3$OD) δ ppm; 6.82 (d, 2H, J=8.8 Hz), 6.67 (d. 2H, J=8.8 Hz), 5.36 (s, 1H), 4.17 (dd, 1H, J=6.6, 4.8 Hz), 4.10 (dd, 1H, J=4.8, 0.8 Hz), 4.02 (dt, 1H, J=6.4, 3.7 Hz), 3.73 (dd. 1H, J=11.8, 3.7 Hz), 3.59 (dd, 1H. J=11.8, 6.2 Hz).

$^{13}$C nmr (CD$_3$OD) δ ppm; 151.4(s), 143.3(s), 119.1(d), 117.96(d), 108.2(d), 85.6(d), 76.7(d), 72.6(d), 64.9(t).

Example 7

Preparation of 3-(4-Hydroxyphenyl)-1(3H)-Isobenzofuranone-3-(Phen-4-yl) β-D-Ribofuranoside (The Mono Phenolphthalein Glycoside of D-Ribose)

Stage 1.—Preparation of 3-(4-Hydroxyphenyl)-1(3H)-Isobenzofuranone-3-(Phen-4-yl)2,3,5-Tri-O-Benzoyl-β-D-Ribofuranoside A suspension of 1-O-acetyl-2,3,5-tri-O-benzoyl-β-D-ribofuranose (545 mg, 1.08 mmol). phenolphthalein (702 mg, 2.21 mmol) and boron trifluoride diethyletherate (153 mg, 1.08 mmol, 136 μl) in dry dichloromethane (6 ml) was stirred for 3 hours at room temperature under argon. More phenolphthalein (611 mg, 1.92 mmol) was added and after a further 3.5 hours was worked-up as described in Stage 1 of Example 2 and purified by flash chromatography on silica gel (eluant 7% acetone in toluene). The product (85 mg, 10%) was obtained as a pale yellow oil.

Stage 2.—Preparation of 3-(4-Hydroxyphenyl)-1(3H)-Isobenzofuranone-3-(Phen-4-yl)β-D-Ribofuranoside The product from Stage 1 (85 mg, 0.11 mmol) and anhydrous potassium carbonate was stirred in methanol (2 ml) for 4 hours then worked-up as in Stage 2 of Example 2. The residue was purified by flash chromatography on silica gel (eluting with 7% methanol in dichlorometbone) to give 32 mg, 64% of a colourless oil as a 4:1 mixture of title compound and the α-anomer of the title compound.

$^1$H nmr (CD$_3$OD) δ ppm; 7.99 (3,0.21H), 7.89 (d. 0.79H). 7.76 (t. 0.79H), 7.63–7.57 (m, 2H), 7.46 (t, 0.21H), 7.22 (d, 2H), 7.08 (d, 2.58H), 7.00 (d. 1.42H). 6.74 (d, 2H), 5.63 (d, 0.21H, J=4.4 Hz, H-1 for α-anomer), 5.54 (s, 0.79H, H-1 for β-anomer), 4.21–4.02 (m, 3H). 3.73–3.64 (m, 1H), 3.56–3.30 (m, 1H).

$^3$C nmr (CD$_3$OD) δ ppm; 171.8(s), 159.0(s), 158.3(s). 154.3(s), 135.8(d), 135.7(d), 132.8(s), 130.6(d), 130.4(d), 129.7(d), 129.5(d), 129.4(d), 129.3(d), 126.6(d), 126.3(s), 125.6(d), 118.0(d), 117.3(d), 116.2(d), 106.7(d), 102.2(d), 93.5(s), 87.6(d), 85.8(d), 76.5(d), 73.3(d), 72.3(d), 71.2(d), 64.6(t), 63.2(t).

Example 8

Preparation of 2,3,5-Tri-O-Benzoyl-α,β-D-Ribofuranosyl Chloride

To a solution of 1-O-acetyl-2,3,5-tri-O-benzoyl-β-D-ribofuranose (3.02 g, 5.98 mmol) in dry dichloromethane (100 ml) was added via cannula a dichloromethane solution of titanium tetrachloride (1.13 g, 5.98 mmol, 5.98 ml of a 1M solution). The solution was stirred at room temperature for 1. 5 hours under argon, then washed with water (3×100 ml), dried over anhydrous magnesium sulfate and evaporated in vacuo to give the title compounds as a colourless oil (2.9 g, 1 00%). $^1$H nmr indicated it to be an approximately 1:1 mixture of α:β-anomers.

$^1$H nmr (CDCl$_3$) δ ppm; 8.06–7.81 (m, 6H), 7.55–7.09 (m, 12H), 6.57 (d, 0.5H, J=4.5 Hz, H-1 of α-anomer), 6.20 (s, 0.5H, H-1 of β-anomer), 6.07 (dd, 0.5H,,J 4.6 Hz), 5.91 (d, 0.5H, J=4.5 Hz), 5.78 (dd, 0.5H, J=7.0, 2.9 Hz), 5.48 (dd, 0.5H, J=7.0, 4.6 Hz), 4.96–4.85 (m, 2H), 4.64–4.55 (m, 1H).

Example 9

Preparation of 2-Nitrophenyl β-D-Ribofuranoside

Stage 1.—Preparation of 2-Nitrophenol, Silver Salt

Silver(II) nitrate (849 mg, 5.00 mmol) was dissolved in water (3 ml) and added to a solution of 2-nitrophenol (696 mg, 5.00 mmol) in 10 ml of aqueous sodium hydroxide (200 mg, 5.00 mmol) solution. The precipitate was filtered, washed with diethyl ether and dried in vacuo over phosphorus pentoxide to afford the title compound as an orange powder (1 .10 g, 89%).

Stage 2.—Preparation of 2-Nitrophenyl 2,3,5-Tri-O-Benzoyl-p-D-Ribofuranoside 2,3,5-Tri-O-benzoyl-α,β-D-ribofuranosyl chloride (320 mg, 0.66 mmol, 1 eq), prepared in Example 8, was azeotropically dried with toluene, redissolved in dry toluene (20 ml) and added to an azeotropically dried (with toluene) suspension of the silver salt (332 mg, 1.35 mmol 2 eq) prepared in Stage 1, in toluene (20 ml) and refluxed under argon for 1.5 hours. The mixture was filtered and the solvent evaporated in vacuo to a yellow oil which was further purified by flash chromatography on silica gel (eluting with dichloromethane:hexanes, 5:1 to give the title compound as a gum (226 mg).

Stage 3.—Preparation of 2-Nitrophenyl β-D-Ribofuranoside

The product from Stage 2 was dissolved in methanol (6 ml), the pH adjusted to 11 by the addition of 10% aqueous sodium hydroxide solution and stirred for 16 hrs. Work-up as in Stage 2 of Example 2 followed by purification by flash chromatography on silica gel (eluting with 10% methanol in dichloromethane) afforded the title compound as pale yellow crystals (62 mg, 61%).

$^1$H nmr (CD$_3$OD) δ ppm; 7.78 (dd, 1H, J=8.1, 1.6 Hz). 7.56 (dt. 1H, J=7.9, 1.6 Hz), 7.42 (dd, 1H, J=8.5, 0.9Hz), 7.12 (dt, 1H, J=8.3, 1.1 Hz), 5.68 (s, 1H), 4.22 (m, 2H), 4.10 (dt, 1H. J=6.6, 3.5 Hz), 3.74 (dd, 1H, J=11.9, 3.5Hz), 3.55 (dd, 1H, J=11.9, 6.6 Hz).

$^{13}$C nmr (CD$_3$OD) δ ppm, 150.6(s), 142.2(s), 134.9(d), 125.9(d), 122.8(d), 118.7(d), 107.2(d), 86.2(d), 76.3(d), 72.2 (d), 64.6(t).

Example 10

Preparation of 4-Methylcoumarin-7-yl β-D-Ribofuranoside (4-Methylumbelliferyl β-D-Riboside)

Stage 1.—Preparation of 7-Hydroxy-4-Methylcoumarin, Silver Salt

This compound was prepared from 471 mg of 7-hydroxy-4-methylcoumarin by the method described in Stage 1 of Example 9 to give the title compound as a brown powder (652 mg, 86%).

Stage 2.'Preparation of 4-Methyl Coumarin-7-yl 2,3,5-Tri-O-Benzoyl-β-D-Ribofuranoside The title compound was prepared by reaction of the product of Stage 1 with the chloride from Example 8 by the method described in Stage 2 of Example 9 but with a reflux time of 30 hrs. The product was purified by flash chromatography on silica gel (eluting with 1% acetone in dichloromethane) to afford 102 mg, 25% of a yellow oil.

Stage 3.—Preparation of 4-Methylcoumarin-7-yl β-D-Ribofuranoside

The product from Stage 2, (102 mg, 0.16 mmol) was dissolved in methanol (7 ml) and treated with sodium methoxide (35 mg, 0.66 mmol, i.e. 140 mg of a 25% solution in methanol). After 4 hrs the reaction was worked-up as described in Stage 2 of Example 2. Purification by flash chromatography (eluting with 10% methanol in dichloromethane) gave the title compound as a colourless solid (24 mg, 47%).

$^1$H nmr, (d$_6$-DMSO) δ ppm; 7.70 (d, 1H), 6.98 (m, 2H), 6.24 (s, 1H), 5.60 (s, 1H), 5.39 (d, 1H), 5.05 (d, 1H), 4.66 (t, 1H), 4.05 (m, 2H), 3.93 (m, 1H), 3.53 (m, 1H), 3.40 (m, 1H), 2.40 (s, 3H).

$^{13}$C nmr (d$_6$-DMSO) δ ppm; 161.1 (s), 160.5 (s), 159.6 (s), 154.5 (s), 127.7 (d), 115.2 (S), 114.6 (d), 112.8 (d), 106.4 (d), 104.5 (d), 86.1 (d), 75.8 (d), 71.7 (d), 63.8 (t), 19.3 (q).

Example 11

Preparation of 3-Pyridyl β-D-Ribofuranoside

Stage 1.—Preparation of 3-Hydroxypyridine, Silver Salt

This compound was prepared from 500 mg of 3-hydroxypyridine by the method described in Stage 1 of Example 9 to give the title compound as a cream-coloured product (996 mg, 94%).

Stage 2.—Preparation of 3-Pyridyl 2,3,5-Tri-O-Benzoyl-D-Ribofuranoside

The title compound was prepared by reacting the product from Stage 1 with the chloride from Example 8 by the method described in Stage 2 of Example 9 but with a reflux time of 24 hours. The product was purified by flash chromatography on silica gel (eluting with 4% acetone in dichloromethane) to afford 144 mg, 44% of a yellow oil.

Stage 3.—Preparation of 3-Pyridyl β-D-Ribofuranoside

The product from Stage 2 (120 mg, 0.22 mmol) was dissolved in methanol (10 ml), 10% aqueous sodium hydroxide solution added to bring the pH to 11, then stirred for 21 hours. Work-up as described in Stage 2 of Example 2 followed by flash chromatography on silica gel (eluting with 10% methanol in dichloromethane) gave the product as a yellow gum (29 mg, 57%).

$^1$H nmr (D$_2$O) δ ppm; 8.43 (m, 2H), 7.75–7.72 (m, 1H), 7.66–7.58 (m, 1H) 5.90 (s, 1H), 4.59–4.53 (m, 2H), 4.35–4.29 (m, 1H), 3.98 (dd, 1H, J=12.4. 3.3 Hz), 3.78 (dd, 1H, J=12.4, 6.2 Hz) (referenced to HOD at 4.94 ppm).

$^{13}$C nmr (D$_2$O) δ ppm; 155.6(s), 145.4(d), 141.1(d), 134.2(s), 131.7(s), 131.2(s), 128.2(d), 127.9(d), 107.9(d), 86.7(d), 77.5(d), 73.4(d), 65.3(t);

Example 12

Preparation of 4-Pyridyl β-D-Ribofuranoside

Stage 1.—Preparation of 4-Hydroxypyridine, Silver Salt

This compound was prepared from 243 mg of 4-hydroxypyridine by the method described in Stage 1 of Example 9 to give the title compound as a brown powder (428 mg, 83%).

Stage 2.—Preparation of 4-Pyridyl 2,3,5-Tri-O-Benzoyl-β-D-Ribofuranoside

The title compound was prepared by reacting the product from Stage 1 with the chloride from Example 8 by the method described in Stage 2 of Example 9 but with a reflux time of 3 days. The product was purified by flash chromatography on silica gel (eluting with 4% acetone in dichloromethane) to afford the product as a colourless solid (112 mg, en 38%).

Stage 3.—Preparation of 4-Pyridyl β-D-Ribofuranoside

The product from Stage 2 (112 mg, 0.21 mmol) was dissolved in methanol (5 ml), the pH was adjusted to 11 with 10% aqueous sodium hydroxide solution and the mixture was then stirred for 24 hours. Work-up as in Stage 2 of Example 2 then purification by flash chromatography on silica gel (eluting with 15% methanol in dichloromethane) gave the title compound as a colourless solid (15 mg, 32%).

$^1$H nmr (CD$_3$OD) δ5 ppm; 8.25 (br.d, 2H), 6,96 (d, 2H, J=6.3 Hz), 5.57 (s, 1H), 4.14–4.09 (m, 2H), 3.99 (dt, 1H, J=6.0, 3.5 Hz), 3.61 (dd, 1H, J=12.0, 3.4 Hz), 3.40 (dd, 1H, J=12.0, 6.0 Hz).

$^{13}$C nmr (CD$_3$OD) δ ppm, 165.1(s), 151.2(d), 113.3(d), 106.0(d), 86.2(d), 76.3(d), 72.0(d), 64.1(t).

Example 13

Preparation of 2-(5-Nitropyridyl) β-D-Ribofuranoside

Stage 1.—Preparation of 2-Hydroxy-5-Nitropyridine, Silver Salt

This compound was prepared from 295 mg of 2-hydroxy-5-nitropyridine by the method described in Stage 1 of Example 9 to give the title compound as a green solid (397 mg, 76%).

Stage 2.—Preparation of 2-(5-Nitropyridyl) 2,3,5-Tri-O-Benzoyl-β-D-Ribofuranoside The title compound was prepared by reacting the compound from Stage 1 with the chloride from Example 8 by the method described in Stage 2 of Example 9 but with a reflux time of 4 hours. The product was purified by flash chromatography on silica gel (eluting with dichloromethane:hexanes, 4:1) to afford the title compound as colourless crystals (220 mg, 68%).

Stage 3.'Preparation of 2-(5-Nitropyridyl) β-D-Ribofuranoside

The product from Stage 2 (220 mg, 0.35 mmol) was dissolved in methanol (7 ml), 10% aqueous sodium hydroxide solution was added to adjust the pH to 11 and the mixture was stirred 69 hours. Work-up as in Stage 2 of Example 2 then flash chromatography on silica gel (eluting with 5% methanol in dichloromethane) gave the title compound as a pale yellow solid (10 mg, 10%).

H nmr (CD$_3$OD) δ ppm; 9.05 (d, 1H, J=2.8 Hz), 8.48 (dd. 1H, J=9.1, 2.8 Hz), 6.96 (d, 1H, J=9.2 Hz), 6.39 (s, 1H), 4.27 (dd, 1H, J=7.2, 4.7 Hz). 4.19 (d, 1H, J=4.7 Hz), 4.07 (ddd, 1H, J=7.2, 5.7, 3.3 Hz), 3.76 (dd, 1H. J=12.1, 3.3 Hz), 3.58 (dd, 1H, J=12.1, 5.7 Hz).

$^{13}$C nmr (CD$_3$OD) δ ppm; 166.8(s), 145.3(d), 141.5(s), 135.7(d), 112.7(d), 104.6(d), 85.9(d), 76.0(d), 71.7(d), 63.7 (t).

Example 14

Preparation of 5-Quinolyl β-D-Ribofuranoside

Stage 1.—Preparation of 5-Hydroxyquinoline, Silver Salt

This compound was prepared from 236 mg of 5-hydroxyquinoline by the method described in Stage 1 of Example 9 to give the title compound as a black powder (373 mg, 91%).

Stage 2.—Preparation of 5-Quinolyl 2,3,5-Tri-O-Benzoyl-β-D-ribofuranoside

The title compound was prepared by reaction of the product of Stage 1 with the chloride from Example 8 by the method described in Stage 2 of Example 9 but with a reflux time of 26.5 hours. The filtrate from the reaction was washed with 10% aqueous sodium hydroxide solution then purified by flash chromatography on silica gel (eluting with ethyl acetate:hexanes, 4:6) to afford the crude title compound as a yellow oil (48 mg).

Stage 3.—Preparation of 5-Quinolyl β-D-Ribofuranoside

The product from Stage 2 (48 mg, 0.08 mmol) was dissolved in methanol (1 ml) and stirred 3 hours with anhydrous potassium carbonate (18 mg). Work-up as in Stage 2 of Example 2 followed by flash chromatography on silica gel (eluting with 10% methanol in dichloromethane) gave the title compound as a pale yellow solid (11 mg, 50%).

$^1$H nmr (CD$_3$OD+D$_2$O) δ ppm; 8.83 (dd, 1H, J=4.3, 1.6 Hz), 8.63 (dd, 1H, J=8.5, 1.6 Hz), 7.70–7.68 (m, 2H), 7.53 (dd, 1H, J=8.5. 4.4 Hz), 7.27 (dd, 1H, J=5.8, 3.0 Hz), 5.81 (s, 1H), 4.43–4.38 (m, 2H), 4.17 (dt, 1H, J=5.9, 3.7 Hz), 3.78 (dd, 1H, J=12.0, 3.6 Hz), 3.59 (dd, 1H, J=12.0, 3.7 Hz).

$^{13}$C nmr (CD$_3$OD+D$_2$O) δ ppm; 153.4(s), 151.5(d), 149.4 (s), 133.0(d). 131.3(d). 122.5(s), 122.4(d), 122.0(d), 110.3 (d), 107.0(d), 85.8(d), 76.6(d), 72.4(d), 64.4(t).

Example 15

Preparation of β-D-Ribofuranoside of Luminol

Stage 1.—Preparation of 3-Aminophthalhydrazide, Silver Salt

This compound was prepared from 423 mg of 3-aminophthalhydrazide (luminol) by the method described in Stage 1 of Example 9 to give the title compound as a light green powder (575 mg).

Stage 2.—Preparation of 2,3,5-Tri-O-Benzoyl β-D-Ribofuranoside of Luminol

The title compound was prepared by reaction of the product of Stage 1 with the chloride from Example 8 by the method described in Stage 2 of Example 9 but with a reflux time of 2 hrs. Work-up as in Stage 2 of Example 9 followed by flash chromatography on silica gel (eluting with ethyl acetate:hexanes, 7:13) gave the title compound as a yellow gum (155 mg, 17%).

Stage 3.—Preparation of the β-D-Ribofuranoside of Luminol

The product from Stage 2 (129 mg, 0.21 mmol) and anhydrous potassium carbonate were stirred in methanol (2.5 ml) for 3.5 hours then worked-up as in Stage 2 of Example 2. The residue was purified by flash chromatography on silica gel (eluting with 15% methanol in dichloromethane) to give the title compound as a pale yellow oil (35 mg, 55%).

$^1$H nmr (CD$_3$OD)) δ ppm; 7.47 (t, 1H, J=8.0 Hz), 7.01 (d, 1H, J 7.6 Hz), 6.92 (d, 1H, J=8.1 Hz), 6.20 (s, 1H), 4.34 (dd, 1H, J=7.1, 4.7 Hz), 4.26 (d, 1H, J=4.6 Hz), 4.13 (dt, 1H, J=6.5, 3.3 Hz), 3.81 (dd, 1H, J=12.0, 3.2 Hz), 3.62 (dd. 1H, J=12.0, 6.0 Hz).

$^{13}$C nmr (CD$_3$OD) δ ppm; 164.0(s), 152.2(s), 151.3(s), 135.6(d), 127.3(s), 118.2(s), 111.8(s), 110.6(d), 104.2(d), 85.7(d), 76.0(d), 72.0(d), 64.2(t).

Example 16

Preparation of 2-Deoxy-3,5-di-O-Toluoyl-α-D-Erythro-Pentofuranosyl Chloride

A solution of 2-deoxy-D-ribose (5.00 g. 37.3 mmol) in dry methanol (95 ml) was treated with dry methanol (95 ml) to which acetyl chloride (0.85 ml) had been added. The mixture was stirred for 10 minutes, pyridine (15 ml) was then added and the mixture was evaporated in vacuo to a yellow oil. The residue was dissolved in dry pyridine (30 ml). cooled to 0° C. and p-toluoyl chloride (12.69 g, 82.1 mmol, 10.8 ml) was added. The mixture was allowed to warm to room temperature and stirred overnight. The reaction mixture was partitioned between ethyl acetate (500 ml) and 10% aqueous sulfuric acid (300 ml), and the organic layer was separated and washed with saturated aqueous sodium bicarbonate solution, dried over anhydrous magnesium sulfate and evaporated in vacuo to a yellow oil. The oil was dissolved in glacial acetic acid (100 ml) to which 5.96 g of hydrogen chloride had been added. After 30 minutes the resulting crystalline solid was filtered, washed with cold diethyl ether and dried to yield the title compound (6.9 g). A portion of this product (2.02 g) was recrystallized from hot toluene to afford the title compound as colourless crystals (1.90 g).

$^1$H nmr (CDCl$_3$) δ ppm; 7.99 (d, 2H, J 8.2 Hz), 7.90 (d. 2H, L =8.2 Hz), 7.25 (m, 4H), 6.47 (d, 1H, J=5.0 Hz), 5.56 (dd, 1H, J=7.2, 2.8 Hz), 4.86 (m. 1H), 4.68 (dd, 1H, J=12.1, 3.2 Hz), 4.59 (dd, 1H, J=12.1, 4.3 Hz), 2.92–2.82 (m. 1H). 2.74 (d. 1H, J=14.8 Hz), 2.42 (s, 3H), 2.41 (s, 3H).

$^{13}$C nmr (CDCl$_3$) δ ppm; 166.4(s), 166.1(s), 144.3(s), 144.0(s), 129.9(d), 129.7(d), 129.23(d), 129.20(d), 129.1(d), 126.8(s), 126.7(s), 95.3(d). 84.7(d), 73.6(d), 63.5(t), 44.5(t), 21.71(q), 21.67(q).

Example 17

Preparation of p-Nitrophenyl 2-Deoxy-β-D-Erythro-Pentofuranoside

Stage 1.—Preparation of p-Nitrophenyl 2-Deoxy-3,5-di-O-Toluoyl-β-D-Erythro-Pentofuranoside p-Nitrophenol (178 mg, 1.28 mmol) and sodium hydride (64 mg of a 60% dispersion in mineral oil, 1.6 mmol) were stirred together in dry dimethylformamide (4 ml) at room temperature for 30 minutes then the chloride (416 mg, 1.07 mmol) from Example 16 was added. The mixture was stirred for a further 3 hours, then water (100 ml) was added and the mixture was evaporated in vacuo. The residue was purified by flash chromatography on silica gel (eluting with 20% ethyl acetate in hexanes) to give a pale yellow oil which crystallized from a mixture of chloroform and hexanes to give the title compound as a colourless solid (190 mg, 36%).

Stage 2.—Preparation of p-Nitrophenyl 2-Deoxy-β-D-Erythro-Pentofuranoside

The product from Stage 1 (147 mg, 0.30 mmol) and anhydrous potassium carbonate (105 mg) were stirred together in methanol (4 ml ) for 5 hours. The mixture was evaporated in vacuo and the residue purified by flash chromatography on silica gel (eluting with 7% methanol in dichloromethane). The title compound was obtained as a yellow solid (46 mg, 61%).

$^1$H nmr (CD$_3$OD) δ ppm; 8.18 (d, 2H, J=9.3 Hz), 7.16 (d, 2H, J=9.3 Hz), 6.01 (dd, 1H, J=5.3, 2.2 Hz), 4.44 (m, 1H), 3.99 (m, 1H), 3.60 (dd, 1H, J=11.6, 5.3 Hz), 3.49 (dd, 1H, J=11.7, 6.3 Hz), 2.50 (ddd, 1H, J=13.7, 6.7. 2.2 Hz), 2.30 (dt, 1H, J=13.8, 5.7 Hz).

$^{13}$C nmr (CD$_3$OD) δ ppm: 163.5(s), 143.2(s), 126.4(d), 117.4(d), 103.6(d), 89.2(d), 72.2(d), 64.2(t), 42.2(t).

Example 18

Preparation of 4-Methylcoumarin-7-yl 2-Deoxy-β-D-Erythro-Pentofuranoside

Stage 1.—Preparation of 4-methylcoumarin-7-yl 2-Deoxy-3,5-di-O-toluoyl-β-D-Erythro-Pentofuranoside 7-Hydroxy-4-methylcoumarin (226 mg, 1.28 mmol) and sodium hydride (64 mg of a 60% dispersion in mineral oil, 1.6 mmol) were stirred at room temperature for 30 minutes in dry dimethylformamide (4 ml). Then the chloride (423 mg, 1.09 mmol) from Example 16 was added and after 24 hours the mixture was processed as in Stage 1 of Example 17 and the product isolated by flash chromatography on silica gel (eluting with 2% acetone in dichloromethane) to afford an oil which crystallized from hot methanol as colourless crystals (305 mg, 53%). $^1$H nmr indicated them to be a 91:9 mixture of the title compound and its α-anomer.

Stage 2.—Preparation of 4-Methylcoumarin-7-yl 2-Deoxy-β-D-Erythro-Pentofuranoside The compound from Stage 1 (280 mg, 0.53 mmol) was stirred in methanol (5 ml) with anhydrous potassium carbonate (213 mg, 1.53 mmol) at room temperature for 63 hours. The reaction mixture was then evaporated in vacuo and the product was isolated by flash chromatography on silica gel (eluting with 7% methanol in dichloromethane). The residue obtained was recrystallized from methanol-chloroform to afford the title compound as colourless needles (64 mg, 41%).

$^1$H nmr (d$_6$-DMSO) δ ppm; 7.68 (d, 1H), 6.99 (m. 2H), 6.23 (d, 1H). 6.02 (dd, 1H), 5.20 (d, 1H), 4.70 (t, 1H), 4.28 (m, 1H), 3.85 (m, 1H), 3.42 (m. 1H), 3.28 (m, 1H), 2.40 (d, 3H), 2.37 (m, 1H), 2.20 (m, 1H).

$^{13}$C nmr (d$_6$-DMSO) δ ppm, 161.3 (s), 160.9 (s), 155.5 (s), 154.5 (s), 127.6 (d), 115.0 (s), 114.7 (d), 112.7 (d), 104.6 (d), 103.4 (d), 89.4 (d), 71.6 (d), 63.8 (t), 42. 2 (t), 19.3 (q).

Example 19

Preparation of 3-Carboxamido-6-Pyridyl β-D-Ribofuranoside

Stage 1.—Preparation of 6-Hydroxynicotinamide

A solution of 6-hydroxynicotinic acid (1.00 g, 7.19 mmol) and concentrated sulfuric acid (0.47 ml) in methanol (80 ml) was refluxed for 10 hours then poured into water and sodium bicarbonate (1.45 g) was added. The solvents were evaporated in vacuo and the residue was purified by flash chromatography on silica gel (eluting with 10% –20% methanol in dichloromethane) to give 6-hydroxynicotinic acid, methyl ester as a colourless solid (996 mg, 90%). The product was dissolved in concentrated aqueous ammonia solution and heated at 60° C. for 10 hours. Evaporation of the solvent in vacuo left a solid which was recrystallized from water to give 371 mg, 61% of the title compound as colourless needles.

Stage 2.—Preparation of 6-Hydroxynicotinamide, Silver Salt

This compound was prepared from 247 mg of 6-hydroxynicotinamide by the method described in Stage 1 of Example 9 to give the title compound as a peach-coloured powder (430 mg 98%).

Stage 3.—Preparation of 3-Carboxamido-6-Pyridyl 2,3,5-Tri-O-Benzoyl-β-D-Ribofuranoside The title compound was prepared by reaction of the product of Stage 2 with the chloride of Example 8 by the method described in Stage 2 of Example 9 but with a reflux time of 3 days then 3.5 days at room temperature. The product was purified by flash chromatography on silica gel (eluting with 13% acetone in dichloromethane) to afford 82 mg, 24% of the title compound as a yellow oil.

Stage 4.—Preparation of 3-Carboxamido-6-Pyridyl β-D-Ribofuranoside

The product from Stage 3 (82 mg, 0.14 mmol) was stirred with anhydrous potassium carbonate (20 mg, 0.15 mmol) in methanol (10 ml) at room temperature for 19 hours. The mixture was concentrated in vacuo then purified by flash chromatography on silica gel (eluting with 20% methanol in dichloromethane) affording the title compound as a pale orange oil (22 mg, 58%).

$^1$H nmr (CD$_3$OD) δ ppm; 8.67 (d, 1H, J=2.1 Hz), 8.17 (dd, 1H, J=8.7, 2.5 Hz), 6.88 (dd, 1H, J=8.9, 0.4 Hz), 6.31 (s, 1H), 4.26 (dd, 1H, J=7.1, 4.7 Hz), 4.19 (d, 1H, J=4.8 Hz), 4.07 (dt, 1H, J=6.5, 3.4 Hz), 3.76 (dd, 1H, J=12.0, 3.4 Hz), 3.58 (dd, 1H, J=12.0, 6.0 Hz).

$^{13}$C nmr (CD$_3$OD) δ ppm; 170.0(s), 165.6(s), 148.6(d), 140.1(d), 125.3(s), 112.0(d), 104.3(d), 85.8(d), 76.2(d), 72.1 (d), 64.2(t).

Example 20

Preparation of 4-Formylphenyl β-D-ribofuranoside

A suspension of 1-O-acetyl-2,3,5-tri-O-benzoylβ-D-ribofuranose (1 g, 2.0 mmol), p-hydroxybenzaldehyde (0.5 g, 4.1 mmol), and boron trifluoride diethyletherate (0.12 ml, 1 mmol) in 20 ml of dry dichloromethane was stirred overnight at room temperature. The solvent was removed in vacuo and the residue extracted with ethyl acetate and brine. The organic layer was dried with sodium sulfate, filtered and the solvents were removed in vacuo. The residue was not purified further, but suspended in methanol and the pH adjusted to 11 with 1.0 N aqueous NaOH. This was stirred and with occasional readjustment of the pH until t.l.c. on silica gel (eluant 1:1 ethyl acetate/hexanes) indicated only material at the solvent front or baseline. Silica gel was added directly to the reaction material and the solvent removed in vacuo. The powder was added to a column of silica gel and purified by flash chromatography with 100% ethyl acetate as eluant. The title compound was obtained as a colourless syrup.

$^1$H nmr 200 MHz (d$_4$-MeOH) δ ppm; 9.90 (1H, s), 7.91 (2H, d), 7.22 (2H, d), 5.73 (1H s), 4.3–4.1 (3H, m), 3.77 (1H, dd), 3.57 (1H, dd).

Example 21

Comparison of Kinetic Parameters for N-Ribohydrolases and Purine Nucleoside Phosphorylase with Nucleosides and Nitrophenylriboside

In this Example kinetic parameters for different enzymes were compared using nitrophenylriboside or a purine substrate. The results are shown in Table 1. Nitrophenylriboside was a good substrate for the inosine-uridine nucleoside hydrolase of the protozoan parasite *Crithidia fasciculata* but not for the guanosine-inosine nucleoside hydrolase from the same species. A nucleoside hydrolase from *Trypanosoma brucei brucei* (IAG-nucleoside hydrolase) was relatively poor for hydrolysing nitrophenylriboside. The *E. coli* and bovine spleen enzymes tested were ineffective in hydrolysing the substrate. The striking ability of one of the protozoan parasite enzymes to hydrolyse the substrate provides the basis for an assay for the protozoan parasites (see Example 22).

Example 22

Assay for Parasites Using Hydrolysis of Nitrophenylriboside

The utility of nitrophenylriboside as a substrate for detecting protozoan infections using the presence of nucleoside hydrolases was tested using blood from mice infected with *Trypanosoma cruzi*, the causative agent of Chagas disease (Table 2). The substrate readily detects the presence of the nucleoside hydrolase in a blood lysate prepared from one microlitre of infected blood. The values obtained from the assay from the infected mice were strikingly elevated above those of the uninfected controls.

Example 23

Comparison of Substrates with Different N-Ribohydrolase Enzymes

The enzymes used were highly purified samples from *Crithidia fasciculata* (IU-nucleoside hydrolase) and *Trypanosoma brucei brucei* (IAG-nucleoside hydrolase), available as stock solutions of approximately 20 mg protein/mL.

Each reaction was conducted in a quartz cuvette with a 1 cm path length, placed in the observation chamber of a UV spectrophotometer, and in a total reaction volume of 600 $\mu$L. The temperature was adjusted by use of a circulating water bath, set so that the cuvette temperature equilibrated to 30° C. in about 5 minutes.

background rate was subtracted in the subsequent calculation of this compound's enzyme-catalyzed reaction rate at this pH.

Reactions were initiated by addition of 2 to 20 $\mu$L aliquots of enzyme solution taken either directly from the stock solution or after dilution in the buffer of the assay mixture, such that absorbance changes of 0.005 to 0.080 per minute were observed for compounds active as substrates. Data were fitted to the Michaelis-Menton equation using kaleidagraph, and the resulting kinetic parameters along with other relevant data are summarized in Table 3.

It can be seen that while the $\beta$-D-ribofuranosides of Examples 1, 9,10, 12, 13 and 19 are all good substrates for the IU-nucleoside hydrolase, only those of Examples 12, 13 and 19 are good substrates for the IAG-nucleoside hydrolase. These substrates can therefore be used to distinguish nucleoside hydrolase isozymes, and consequently provide organism-specific detection.

TABLE 1

Kinetic Parameters for N-Ribohydrolases and Purine Nucleoside Phosphorylase with Nucleosides and Nitrophenyl Riboside[a]

| enzyme | Nitrophenol Riboside[R] (or 5-Phosphate)[P] | | | | Purine substrate[b] | | | |
|---|---|---|---|---|---|---|---|---|
| | $k_{cat}$ ($s^{-1}$) | $K_m$ ($\mu$M) | $k_{cat}/K_m$ ($M^{-1}s^{-1}$) | substrate | $k_{cat}$ ($s^{-1}$) | $K_m$ ($\mu$M) | $k_{cat}/K_m$ ($M^{-1}s^{-1}$) | $k_{cat}/K_m$ ratio |
| IU-nucleoside hydrolase[R,c] | 239 ± 32 | 58 ± 23 | $4.1 \times 10^6$ | inosine | 28 | 380 | $7.6 \times 10^4$ | 54 |
| IAG-nucleoside hydrolase[R,d] | 0.82 ± 0.03 | 560 ± 50 | $1.5 \times 10^3$ | inosine | 34 | 18 | $1.9 \times 10^6$ | $8 \times 10^{-4}$ |
| Gl-nucleoside hydrolase[R,c] | 0.07 ± 0.01 | 468 ± 130 | $1.4 \times 10^2$ | guanosine | 231 | 77 | $3.2 \times 10^6$ | $4 \times 10^{-5}$ |
| AMP nucleosidase[P,e] | 0.0004 ± 0.0001 | 6250 ± 1700 | $6.2 \times 10^{-2}$ | AMP | 27 | 150 | $1.8 \times 10^5$ | $3 \times 10^{-7}$ |
| Purine nucleoside phosphorylase[R,f] | 0.00020 ± 0.00004 | 224 ± 76 | $8.9 \times 10^{-1}$ | inosine | 12 | 19 | $6.3 \times 10^5$ | $1 \times 10^{-6}$ |

[a]The enzymes were highly purified samples from *Crithidia fasciculata*[c,5,6], *Trypanosoma brucei brucei*[d,7], *E coli*[e,8,9] and bovine spleen[f,10]. Assays were at pH 8.0 in 50 mM HEPES, 30° C. For the allosteric AMP nucleosidase, MgATP was present at 100 $\mu$M. Purine nucleoside phosphorylase was assayed for phosphorolysis by including 3 mM phosphate in assay mixtures. The superscripts[R] and [P] refer to nitrophenylriboside and nitrophenylriboside 5-phosphate, respectively, as substrates.
[b]Substrate specificity, for purine substrates, the kinetic constants and their standard errors are available in references 5, 6, 11, 9, 10 and 12. The $k_{cat}/K_m$ ratio compares the $k_{cat}/K_m$ for nitrophenylriboside to that for the indicated purine substrate.

The $\beta$-D-ribofuranoside substrates were dissolved in aqueous buffer: 50 mM CHES for reactions at pH 10, 50 mM HEPES for reactions at pH 8. For reactions catalyzed by the IU-nucleoside hydrolase and for those of the IAG-nucleoside hydrolase with the substrates of Examples 1 and 12, five initial substrate concentrations in the range 0.3–3 times the $K_m$ values were used. For the remaining reactions catalysed by IAG hydrolase, a single substrate concentration of between 100 and 300 $\mu$M was used.

The absorbance of each reaction mixture was monitored at or near the absorption maximum for the phenolic aglycon (as shown in Table 3). Monitoring began 5–10 minutes before the enzyme was added to determine if the substrate was stable under the reaction conditions. Only with 5-nitro-2-pyridyl $\beta$-D-ribofuranoside (Example 13) at pH 10 was hydrolysis observed in the absence of enzyme, and this

TABLE 2

Rate of Hydrolysis of Nitrophenyl Riboside with Control or Infected Mouse Blood

| Sample[a] | rate[b] (pmol/min/mg) |
|---|---|
| uninfected control | 0.7 ± 0.8 (11) |
| infected, *T cruzi* var Brazil | 4.6 ± 0.5 (3) |
| infected, *T cruzi* var Tulahuen | 3.9 ± 0.5 (4) |

[a]Blood samples were obtained from uninfected or infected mice, diluted with an equal volume of 0.5% Triton-X-100 and stored overnight at 5° C. prior to assay.
[b]Reaction mixtures containing 50 mM HEPES pH 8.0 at 30° C. were mixed with 2 $\mu$l of diluted blood sample and the background rates recorded. Reactions were initiated by the addition of nitrophenyl riboside to 0.24 mM. The rate of p-nitrophenolate ion formation was monitored at 400 nm, in reaction mixture of 1.0 ml. The numbers in parentheses are the number of independent rate determinations.

TABLE 3

KINETIC PARAMETERS FOR TWO N-RIBOHYDROLASES WITH VARIOUS β-D-RIBOFURANOSIDES

| Example No. | pKa for Y-OH | ΔOD/ mM, λmax (nm)[3] pH 8.0 | ΔOD/ mM, λmax (nm)[3] pH 10.0 | ε for Y-OH λmax[4] pH 10.0 | IU NH[1] At pH 10 kcat (sec⁻¹)[2] | IU NH[1] At pH 10 Km (μM) | IU NH[1] At pH 10 Ki (μM) | IAG NH[1] rate (min⁻¹, at 200 μM substrate[2]) pH 8.0 | IAG NH[1] rate (min⁻¹, at 200 μM substrate[2]) pH 10.0 | IAG NH[1] At pH 10 kcat (min⁻¹) | IAG NH[1] At pH 10 Km (μM) |
|---|---|---|---|---|---|---|---|---|---|---|---|
| 1 | 7.14 | | 17.0 400 | | 290 | 110 | | | 0.05 | 0.19 | 529 |
| 2 | 9.34 | | 5.04 332 | | .009 at 250 μM | | 7.3 | | <0.05 | | |
| 3 | | | ? | ? | yes but very slow | | 27.7 | | ? | | |
| 4 | 9.87 | | .74 295 | | 0.7 at 1240 μM | | 72 | | <0.02 | | |
| 5 | | 0.64 332 | 1.83 361 | 1.86 360 | 0.5 at 200 μM | | | <0.01 | <0.01 | | |
| 6 | | | | 2.02 298 | <0.01 | | | | | | |
| 7 | | | 29.2 553 | 19.2 553 | 10 at 200 μM | | | <0.01 | <0.01 | | |
| 9 | 7.23 | | 4.5 415 | | 188 | 164 | | | 0.15 | | |
| 10 | ~8 | | 19.5 361 | | 130 | 31.4 | | | 0.003 | | |
| 11 | | 2.67 311 | 4.3 298 | | 22.1 | 28.5 | | | 0.01 | | |
| 12 | 11 | 6.3 254 | 6.3 254 | | 169 | 650 | | | | 717 | 306 |
| 13 | | | 11.9 367 | 14.8 366 | 100 | 122 | | >100 | >100 | | |
| 14 | | 0.89 343 | 2.80 365 | 2.95 365 | 2 at 200 μM | | | 0.16 | <0.01 | | |
| 15 | | | 2.05 315 | 6.8 349 | 163 | 133 | | <0.01 | <0.03 | | |
| 19 | | | 5.56 298 | | 141 | 369 | | >100 | 24 | | |
| 20 | 7.66 | | 26.0 330 | 26.0 330 | 181 | 149 | | | 0.01 | | |

[1]IU-NH, IU-nucleoside hydrolase from *Crithidia fasciculata*; IAG-NH, IAG-nucleoside hydrolase from *Trypanosoma brucei brucei*.
[2]Where no hydrolysis was apparent, the slope was assumed to be less than 0.0001 ΔOD/min.
[3]Changes in absorbance for the conversion 1 mM of the β-D-ribofuranoside substrate to 1 mM product at the indicated pH and wavelength and for a 1 cm pathlength, calculated from experimentally observed data. The wavelength was the absorbance maximum.
[4]Absorbance determined experimentally for 1 mM solution of the phenolic aglycon at the indicated pH and wavelength, and for a 1 cm pathlength.

Example 24

Detection of *Giardia intestinalis*

*Giardia intestinalis* (Portland 1 strain) was grown for 2 days in TYI-33 medium supplemented with 5 mM arginine, harvested and washed. A suspension containing $2.91 \times 10^8$ cells of Giardia intestinalis in 1 mL of aqueous HEPES buffer (40 mM, pH 7) was mixed with 1 mL of aqueous HEPES buffer (40 mM, pH 7) containing 0.1 mM protease inhibitor E-64 and sonicated (Branson sonicator, duty cycle 40, output 2.5),for 2–3 min in ice. The suspension was then centrifuged in a Beckman microfuge for 10 mins at 4° C., and the supernatant decanted.

A second suspension of $2.91 \times 10^8$ cells of *Giardia intestinalis* in 1 mL of aqueous HFPES buffer (40 mM, pH 7) was mixed with 1 mL of 0.5% aqueous Triton X-100, left at 4° C. overnight, and the supernatant was decanted.

Aliquots (between 2 and 100 μL) of each of these supernatants were made up to a volume of 1 mL of water containing 50 mM HEPES buffer at pH 8, 0.24 mM 4-nitrophenyl β-D-ribofuranoside or 4-pyridyl β-D-ribofuranoside. The release of the aglycon was monitored by absorption spectrometry at 400 nm or 253 nm, respectively. The 5 μL aliquots were sufficient for ready measurement of increased absorbance. The activity of the supernatant was stable to storage at 4° C. for 6 days.

The rates of reaction were approximately the same for both substrates. For 4-nitrophenyl β-D-ribofuranoside, with an extinction coefficient for 4-nitrophenol of 14,000. the activity was 470 nmoles.min⁻¹ per $10^8$ cells, corresponding to an activity for the enzyme of 70 nmoles.min⁻¹.(mg protein)⁻¹. For 4-pyridyl β-D-ribofuranoside, the activity was 210 nmoles.min⁻¹ per $10^8$ cells, corresponding to an activity for the enzyme of 31 nmoles.min$^{-1}$. (mg protein). Protein was determined by Lowry method (ie Folin reaction).

Example 25

Detection of *Trypanosoma vaginalis*

*Trypanosoma vaginalis* was grown for 2 days in TYM medium, harvested, and washed. An extract of a suspension containing 7.76×10$^7$ cells.mL$^{-1}$ *Trypanosoma vaginalis* in aqueous HEPES buffer (40 mM, pH 7) was prepared using Triton X-100 as described for *Giardia intestinalis* in Example 24.

The ability of the extract to hydrolyse substrates was determined as in Example 24. For 4-nitrophenyl β-D-ribofuranoside, the activity was 165 nmoles.min$^{-1}$ per 10$^8$ cells, corresponding to an activity for the enzyme of 9 nmoles.min$^{-1}$.(mg protein)$^{-1}$. For 4-pyridyl β-D-ribofuranoside, the activity was 74 nmoles.min$^{-1}$ per 10$^8$ cells, corresponding to an activity for the enzyme of 4 nmoles.min$^{-1}$.(mg protein)$^{-1}$.

REFERENCES

1. Lee H C; Galione, A; Walseth, T F Vitamins and Hormones 1994, 48, 199.
2. Mentch, F; Parkin, D W; Schramm, V L Biochemistry 1987, 26, 921.
3. Horenstein, B A; Parkin, D W; Estupinan, B; Schramm, V L Biochemistry 1991, 30, 10788.
4. Kline, P C; Schramm, V L Biochemistry 1995, 34, 1153.
5. Parkin D W; Horenstein, B A: Abdulah D R; Estupinan B; Schramm, V L J Biol Chem 1991, 266, 20658.
6. Estupinan, B; Schramm V L J Biol Chem 1994, 269, 23068.
7. Parkin, D W; Schramm V L Biochemistry 1995, 34, 13961.
8. Leung, H B; Kvalnes-Krick K L; Myer S L; deRiel, J K; Schramm V L Biochemistry 1989, 28, 8726.
9. Leung, H B; Schramm V L J Biol Chem 1980, 255, 10867.
10 Kline, P C: Schramm V L Biochemistry 1992 31, 5964.
11. Parkin, D W, J Biol Chem 1996, 271, 21713.
12. Kline, PC; Scharnm V L Biochemistry 1993, 32, 13212.

Aspects of the invention have been described by way of example only and it should be appreciated that modifications and additions thereto may be made without departing from the scope of the invention.

What is claimed is:

1. A method for detecting a nucleoside hydrolase or a nucleoside phosphorylase in a sample comprising the steps of:
    (a) contacting said sample with a chromogenic substrate having the formula:

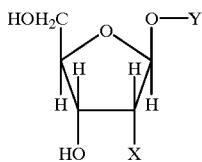

wherein X is OH or H, and Y is the residue of Y—OH, wherein Y—OH is a chromophore or a compound readily converted to a chromophore, and
    (b) detecting formation of a chromophore product or an ion thereof, wherein direction of the chromophore product or ion thereof indicates the presence of a nucleoside hydrolase or a nucleoside phosphorylase in the sample.

2. The method of claim 1, wherein said sample is a biological fluid sample.
3. The method of claim 2, wherein said sample is a blood or serum sample.
4. The method of claim 1, wherein said sample is obtained from a mammal.
5. The method of claim 4, wherein said mammal is a human, bovine, a pig, a goat, a sheep, or a horse.
6. The method of claim 1, wherein said nucleoside hydrolase or said nucleoside phosphorylase is from a parasite.
7. The method of claim 6, wherein said parasite is a Trypanosoma, a Giardia, a Trichomona, a Leishmania, a Crithidia, a Herpetomonas, or a Leptomonas.
8. The method of claim 7, wherein said parasite is a Trypanosoma.
9. The method of claim 8, wherein said Trypanosoma is *Trypanosoma cruzi*.
10. The method of claim 1, wherein said chromophore product is detected by absorption of visible light, by absorption of UV light, and/or by altering pH.
11. The method of claim 1, wherein said chromophore product is a colored or fluorescent compound.
12. The method of claim 11, wherein said chromophore product is phenolphthalein, p-nitrophenol, thymolphthalein, 2-nitrophenol, 2-hydroxy-5-nitropyridine, 6-hydroxynicotinamide or 2-hydroxypyridine-4-carboxamide, 4-methylumbelliferone or fluorescein.
13. The method of claim 1, wherein said chromophore product is detected by reaction of Y—OH with a diazonium salt.
14. The method of claim 13, wherein Y—OH is α-naphthol.
15. The method of claim 1 where the chromogenic substrate is selected from 2-nitrophenyl β-D-ribofuranoside, 4-methylumbelliferyl β-D-ribofuranoside, 3-pyridyl β-D-ribofuranoside, 4-pyridyl β-D-ribofuranoside, 2-(5-nitropyridyl) β-D-ribofuranoside, β-D-ribofuranoside of luminol, 3-carboxamido-6-pyridyl β-D-ribofuranoside and 4-formylphenyl β-D-ribofuranoside.
16. The method of claim 1, wherein said chromogenic substrate is p-nitrophenyl β-D-ribofuranoside.
17. A method for detecting a parasite which expresses a nucleoside hydrolase or a nucleoside phosphorylase in a sample comprising the steps of:
    (a) contacting said sample with a chromogenic substrate having the formula

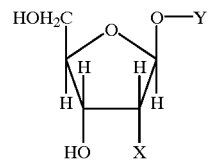

wherein X is OH or H, and Y is the residue of Y—OH, wherein Y—OH is a chromophore or a compound readily converted to a chromophore, and
    (b) detecting formation of a chromophore product or an ion thereof, wherein detection of the chromophore product or ion thereof indicates the presence of a parasite which expresses a nucleoside hydrolase or a nucleoside phosphorylase in the sample.

18. The method of claim 17, wherein said sample is a biological fluid sample.

19. The method of claim 18, wherein said sample is a blood or serum sample.

20. The method of claim 17, wherein said sample is obtained from a mammal.

21. The method of claim 20, wherein said mammal is a human, a bovine, a pig, a goat, a sheep, or a horse.

22. The method of claim 17, wherein said parasite is a Trypanosoma, a Giardia, a Trichomona, a Leishmania, a Crithidia, a Herpetomonas, or a Leptomonas.

23. The method of claim 22, wherein said parasite is a Trypanosoma.

24. The method of claim 22, wherein said Trypanosoma is *Trypanosoma cruzi*.

25. The method of claim 17 wherein said parasite is a Toxoplasma or a Neophora.

26. A method of claim 17 wherein parasite is *Giardia intestinalis* or a Trichomona.

27. The method of claim 17, wherein said chromophore product is detected by absorption of visible light, by absorption of UV light, and/or by altering pH.

28. The method of claim 27, wherein said chromophore product is a colored or fluorescent compound.

29. The method of claim 28, wherein said chromophore product is phenolphthalein, p-nitrophenol, thymolphthalein, 2-nitrophenol, 2-hydroxy-5-nitropyridine, 6-hydroxynicotinamide or 2-hydroxypyridine4-carboxamide, 4-methylumbelliferone or fluorescein.

30. The method of claim 17, wherein said chromophore product is detected by reaction of Y—OH with a diazonium salt.

31. The method of claim 30, wherein Y—OH is α-naphthol.

* * * * *

UNITED STATES PATENT AND TRADEMARK OFFICE
CERTIFICATE OF CORRECTION

| | | |
|---|---|---|
| PATENT NO. | : 6,379,911 B2 | Page 1 of 1 |
| APPLICATION NO. | : 09/125808 | |
| DATED | : April 30, 2002 | |
| INVENTOR(S) | : Vern L. Schramm et al. | |

It is certified that error appears in the above-identified patent and that said Letters Patent is hereby corrected as shown below:

Column 1,
Line 3, add the following paragraph:
-- STATEMENT OF GOVERNMENT SUPPORT The invention disclosed herein was made with U.S. Government support under grant number GM41916 from the National Institutes of Health, U.S. Department of Health and Human Services.
Accordingly, the U.S. Government has certain rights in this invention. --.

Signed and Sealed this

Sixth Day of February, 2007

JON W. DUDAS
*Director of the United States Patent and Trademark Office*